United States Patent [19]

Mayer et al.

[11] Patent Number: 4,603,202
[45] Date of Patent: Jul. 29, 1986

[54] FLUORAN COLORANTS FOR RECORDING SYSTEMS

[75] Inventors: Udo Mayer, Frankenthal; Andreas Oberlinner, Ludwigshafen, both of Fed. Rep. of Germany

[73] Assignee: BASF Aktiengesellschaft, Rheinland-Pfalz, Fed. Rep. of Germany

[21] Appl. No.: 660,128

[22] Filed: Oct. 12, 1984

[30] Foreign Application Priority Data

Oct. 14, 1983 [DE] Fed. Rep. of Germany ....... 3337387

[51] Int. Cl.$^4$ ................. C07D 407/12; C07D 493/10; C07D 413/00; C07D 311/78; C07D 405/12
[52] U.S. Cl. ..................... 544/150; 546/15; 548/407; 549/224; 544/129; 544/141; 544/143
[58] Field of Search ............. 548/407; 546/15; 544/151, 150, 129, 141, 143; 549/224, 225

[56] References Cited

U.S. PATENT DOCUMENTS

| | | | |
|---|---|---|---|
| 2,800,457 | 7/1957 | Green et al. | 252/316 |
| 2,800,458 | 7/1957 | Green | 252/316 |
| 3,103,404 | 9/1963 | Salvin et al. | 8/64 |
| 3,442,908 | 5/1969 | Orita et al. | 260/335 |
| 3,501,331 | 3/1970 | Kimura et al. | 117/36.2 |
| 3,506,471 | 4/1970 | Kimura et al. | 117/36.2 |
| 3,624,107 | 11/1971 | Lin | 549/225 |
| 3,649,649 | 3/1972 | Orita et al. | 549/225 |
| 3,825,561 | 7/1974 | Akamatsu et al. | 546/15 |
| 3,843,384 | 10/1974 | Adachi et al. | 117/36.9 |
| 3,872,023 | 3/1975 | Baum et al. | 252/316 |
| 3,901,918 | 8/1975 | Koga et al. | 549/224 |
| 3,925,416 | 12/1975 | Akamatsu et al. | 549/224 |
| 3,959,571 | 5/1976 | Yahagi et al. | 428/537 |
| 4,156,682 | 5/1979 | Hotta et al. | 549/224 |
| 4,302,393 | 11/1981 | Garner et al. | 428/307 |
| 4,406,816 | 9/1983 | Sliwka | 428/320.6 |
| 4,436,920 | 3/1984 | Sato et al. | 546/15 |

FOREIGN PATENT DOCUMENTS

| | | |
|---|---|---|
| 842841 | 5/1970 | Canada . |
| 1211393 | 11/1970 | United Kingdom . |
| 1306263 | 2/1973 | United Kingdom . |
| 1339316 | 12/1973 | United Kingdom . |
| 1459417 | 12/1976 | United Kingdom . |
| 2014629A | 8/1979 | United Kingdom . |
| 495905 | 10/1977 | U.S.S.R. . |

OTHER PUBLICATIONS

J.C.S. Chem. Comm., pp. 956 and 957 (1974).

Primary Examiner—Veronica P. Hoke
Attorney, Agent, or Firm—Oblon, Fisher, Spivak, McClelland & Maier

[57] ABSTRACT

Fluorans of the formula (I)

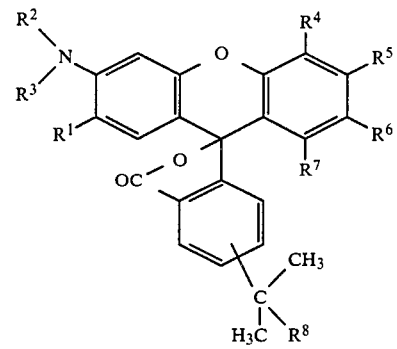

where $R^1$ is hydrogen or methyl, $R^2$ is hydrogen or unsubstituted or substituted alkyl, $R^3$ is hydrogen, unsubstituted or substituted alkyl, cycloalkyl or unsubstituted or substituted phenyl, or

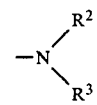

is a 5-membered or 6-membered saturated heterocyclic radical, $R^4$ and $R^5$ independently of one another are each hydrogen, alkyl, alkoxy or halogen, $R^6$ is hydrogen, halogen, alkyl, alkoxy, phenylalkoxy, phenoxy, phenyl or unsubstituted or substituted amino, or is pyrrolidinyl, piperidinyl or morpholinyl, $R^7$ is hydrogen, alkyl or halogen, $R^8$ is $C_1$–$C_5$-alkyl, and the radicals $R^4$ and $R^5$ and/or $R^6$ and $R^7$ together may furthermore each be a —CH═CH—CH═CH— bridge, and the fused-on benzo ring may be further substituted, are used for the preparation of pressure-sensitive and heat-sensitive recording materials.

7 Claims, No Drawings

FLUORAN COLORANTS FOR RECORDING SYSTEMS

The present invention relates to novel fluorans and their use in recording systems.

Fluorans and their use in recording systems have been disclosed (eg. German Laid-Open Application Nos. DOS 2,039,848, DOS 2,422,899 and DOS 2,024,859, German Published Application Nos. DAS 1,671,545 and DAS 1,543,803, British Pat. Nos. 1,211,393 and 2,014,629 and U.S. Pat. Nos. 3,506,471 and 3,959,571).

It is an object of the present invention to provide fluorans which possess better solubility and improved migration properties.

We have found that this object is achieved by fluorans of the present invention.

Accordingly, the present invention relates to fluorans of the general formula I

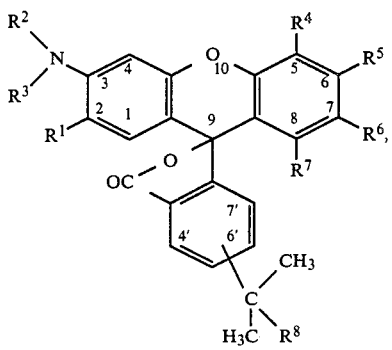

where $R^1$ is hydrogen or methyl, $R^2$ is hydrogen, $C_1$–$C_4$-alkyl, $C_7$- or $C_8$-phenylalkyl cyanoethyl, chloroethyl or alkoxyalkyl having a total of 3 to 5 carbon atoms, $R^3$ is hydrogen, $C_1$–$C_4$-alkyl, $C_7$–$C_{10}$-phenylalkyl, $C_5$–$C_6$-cycloalkyl, cyanoethyl, chloroethyl, alkoxyalkyl having a total of 3 to 5 carbon atoms, or phenyl which is unsubstituted or substituted by $C_1$–$C_4$-alkyl, methoxy, chlorine or bromine, or

is N-pyrrolidinyl, N-piperidinyl, N-morpholinyl or N-isoindolinyl, $R^4$ and $R^5$ independently of one another are each hydrogen, $C_1$–$C_4$-alkyl, $C_1$–$C_4$-alkoxy or halogen, $R^6$ is hydrogen, halogen, $C_1$–$C_{12}$-alkyl, $C_1$–$C_4$-alkoxy, $C_7$–$C_{10}$-phenylalkoxy, phenoxy, phenyl, or a group of the formula

where $X^1$ is hydrogen, $C_1$–$C_4$-alkyl, chloroethyl, alkoxyalkyl having a total of 3 to 5 carbon atoms, $C_7$- or $C_8$-phenylalkyl and $X^2$ is hydrogen, $C_1$–$C_{12}$-alkyl, chloroethyl, $C_5$- or $C_6$-cycloalkyl, alkoxyalkyl having a total of 3 to 5 carbon atoms, $C_7$–$C_{10}$-phenylalkyl, or phenyl which is unsubstituted or substituted by halogen, $C_1$–$C_4$-alkyl, $C_1$–$C_4$-alkoxy, $C_1$–$C_4$-alkylcarbonyl, benzoyl or phenoxy, or is $C_1$–$C_4$-alkoxycarbonyl-$C_1$–$C_3$-alkyl, or carbamyl-$C_1$–$C_3$-alkyl, or

is pyrrolidinyl, piperidinyl or morpholinyl, $R^7$ is hydrogen, $C_1$–$C_4$-alkyl or halogen and $R^8$ is $C_1$–$C_5$-alkyl, and the radicals $R^4$ and $R^5$ and/or $R^6$ and $R^7$ together can each be a —CH=CH—CH=CH— bridge, and the fused-on ring can be unsubstituted or substituted by halogen or by amino which is unsubstituted or monosubstituted or disubstituted by $C_1$–$C_4$-alkyl or $C_7$- or $C_8$-phenylalkyl.

The novel fluorans possess improved solubility in the core compositions or solvents conventionally used in the preparation of microcapsules, and therefore permit greater flexibility in the choice of the solvents. For reasons of toxicity and ecological reasons, the use of halogen-containing solvents, in which the prior art fluorans are readily soluble, is unacceptable for micro-capsules; hence, the better universal solubility of the novel fluorans in other physiologically better tolerated solvents is of great importance. Moreover, a number of novel fluorans exhibit less migration in the base material compared with the prior art fluorans.

The fluorans of the formula I are slightly colored or colorless compounds whose solutions in inert organic solvents, when in contact with electron acceptors, produce colorations in yellow, orange, red, blue, olive or black hues, depending on the substitution of the fluoran. Examples of electron acceptors are carboxylic acids, mineral acids, kaolin, bentonite, activated clay, aluminum silicate, attapulgite or any clay, acidic polymeric materials, such as condensates based on phenols and/or phenolsulfonic acids, and metal oxides or salts, such as zinc oxide, alumina, zinc chloride, iron stearate or cobalt naphthenate.

Because of these properties, the novel compounds (I) can be used as color-producing agents in pressure-sensitive and heat-sensitive recording materials.

For use in pressure-sensitive systems, the fluorans (I), advantageously in the form of solutions in organic solvents, such as chloroparaffins, partially hydrogenated di- or terphenyls, alkylbenzenes, alkylnaphthalenes, alkylated dibenzylbenzene, paraffin oil or mineral oil, or in conventional lower-boiling solvents, such as xylene or toluene, are enclosed in microcapsules, and the base, eg. paper, is coated with these. Under pressure, contact with the electron acceptors results in the production of color at the pressure point.

Suitable methods for the preparation of microcapsules are disclosed in, for example, U.S. Pat. Nos. 2,800,457 and 2,800,458, German Pat. No. 2,119,933 and European Pat. No. 26,914. By means of the method described in U.S. Pat. No. 3,103,404, the novel compounds of the general formula I can also be finely dispersed in wax or an oil/wax mixture, and the base, eg. a film or paper, can be coated with the resulting mixture.

The pressure-sensitive materials obtained can be used for making carbon copies onto papers coated with electron acceptors, and are removed after use, like carbon paper.

The novel fluorans can also be used as color-producing agents in heat-sensitive recording materials which contain a binder, a color-producing agent and an electron acceptor on a base. The structure of such heat-sensitive recording materials and the composition of the layers which produce color under the action of heat have been disclosed (eg. German Laid-Open Application Nos. DOS 2,228,581 and DOS 2,110,854), as have the methods and apparatuses by means of which color production is achieved.

Specific examples of substituents $R^1$ to $R^8$, $X^1$ and $X^2$ for the fluorans of the formula (I) are as follows:

$R^1$ is methyl or, preferably, hydrogen.

$C_1$–$C_4$-alkyl radicals $R^2$, $R^3$, $R^4$, $R^5$, $R^7$ and $X^1$ independently of one another are each methyl, ethyl, n- or i-propyl, or n- or i-butyl.

$C_1$–$C_{12}$-alkyl radicals $R^6$ and $X^2$ are each one of the $C_1$–$C_4$-alkyl radicals stated specifically above, or n-pentyl, n-hexyl, n-octyl, 2-ethylhexyl, nonyl, decyl or dodecyl.

$C_1$–$C_5$-alkyl radicals $R^8$ are methyl, ethyl, propyl, n-butyl, sec.-butyl, pentyl and 2,2-dimethylprop-1-yl, preferably ethyl or 2,2-dimethylprop-1-yl, particularly preferably methyl.

$C_1$–$C_4$-alkoxy radicals $R^4$ and $R^5$ are each methoxy, ethoxy, n- or i-propoxy or n- or i-butoxy.

Alkoxyalkyl radicals $R^2$, $R^3$, $X^1$ and $X^2$ of 3 to 5 carbon atoms are each 2-methoxyethyl, 2-ethoxyethyl, 2-propoxyethyl, 3-methoxypropyl or 3-ethoxypropyl.

Phenylalkyl radicals $R^2$ and $X^1$ are each benzyl, 1-phenylethyl or 2-phenylethyl.

$C_7$–$C_{10}$-phenylalkyl radicals $R^3$, $R^6$ and $X^2$ are each one of the phenylalkyl radicals stated for $R^2$, or 2- or 3-phenylpropyl or 2-, 3- or 4-phenylbutyl.

$C_5$- and $C_6$-cycloalkyl radicals $R^3$ and $X^2$ are each cyclopentyl, methylcyclopentyl or, preferably, cyclohexyl.

Halogen is chlorine, bromine or fluorine, preferably bromine, in particular chlorine.

$R^3$ may furthermore be phenyl which is unsubstituted or substituted by $C_1$–$C_4$-alkyl, methoxy, chlorine or bromine, suitable $C_1$–$C_4$-alkyl radicals being those stated for $R^2$.

$X^2$ may furthermore be phenyl which is unsubstituted or substituted by halogen, $C_1$–$C_4$-alkyl, $C_1$–$C_4$-alkoxy, $C_1$–$C_4$-alkylcarbonyl, benzoyl or phenoxy. Examples of suitable $C_1$–$C_4$-alkyl radicals are those mentioned for $R^2$, and examples of suitable $C_1$–$C_4$-alkoxy radicals are those mentioned for $R^4$. Examples of suitable $C_1$–$C_4$-alkylcarbonyl radicals are acetyl, propionyl, butyryl and valeryl (pentanoyl).

$X^2$ may furthermore be $C_1$–$C_4$-alkoxycarbonyl-$C_1$–$C_3$-alkyl or carbamyl-$C_1$–$C_3$-alkyl, specific examples being methoxycarbonylmethyl, ethoxycarbonylmethyl, ethoxycarbonylethyl, carbamylmethyl and carbamylethyl.

Because of their performance characteristics, preferred fluorans of the formula (I) are those in which $R^8$ is methyl, ethyl or 2,2-dimethylprop-1-yl. Among these, the fluorans in which $R^8$ is $CH_3$ are very particularly preferred.

Because of their performance characteristics, the following fluorans of the formulae (II), (III), (IV) and (V) are preferred:

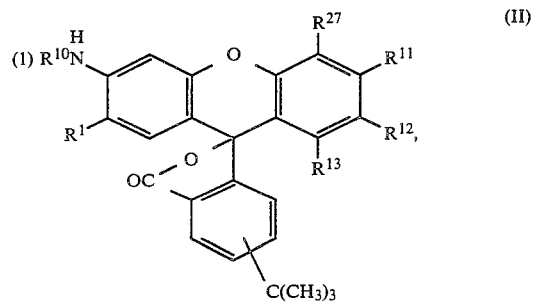

where $R^1$ is hydrogen or methyl, $R^{10}$ is hydrogen, $C_1$–$C_4$-alkyl, cyclohexyl or benzyl, or is phenyl which is unsubstituted or monosubstituted or disubstituted by methyl and/or ethyl and/or monosubstituted by chlorine, bromine or methoxy, $R^{11}$ is hydrogen, chlorine or $C_1$–$C_4$-alkyl, $R^{12}$ is $C_1$–$C_{12}$-alkyl or halogen, and $R^{13}$ and $R^{27}$ are each hydrogen or methyl.

$R^1$ is preferably hydrogen when $R^{10}$ is unsubstituted or substituted phenyl.

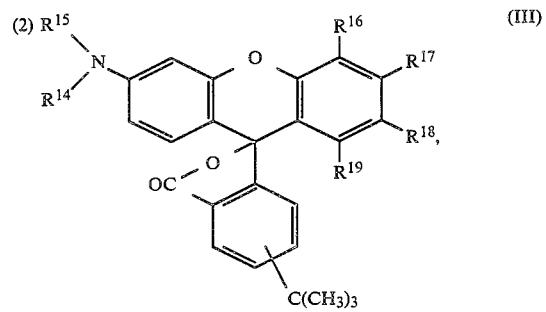

where $R^{14}$ is $C_1$–$C_4$-alkyl, $C_7$- or $C_8$-phenylalkyl or alkoxyalky having a total of 3 to 5 carbon atoms, $R^{15}$ is $C_1$–$C_4$-alkyl, $C_7$–$C_{10}$-phenylalkyl, $C_5$- or $C_6$-cycloalkyl, alkoxyalkyl having a total of 3 to 5 carbon atoms, or phenyl which is unsubstituted or monosubstituted by $C_1$–$C_4$-alkyl, chlorine or bromine, or

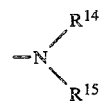

is pyrrolidinyl, piperidinyl or morpholinyl, $R^{16}$ and $R^{17}$ independently of one another are each hydrogen, chlorine or $C_1$–$C_4$-alkyl, $R^{18}$ is hydrogen, $C_1$–$C_{12}$-alkyl, $C_1$–$C_4$-alkoxy, $C_7$–$C_{10}$-phenylalkoxy, phenoxy or halogen and $R^{19}$ is hydrogen or $C_1$–$C_4$-alkyl.

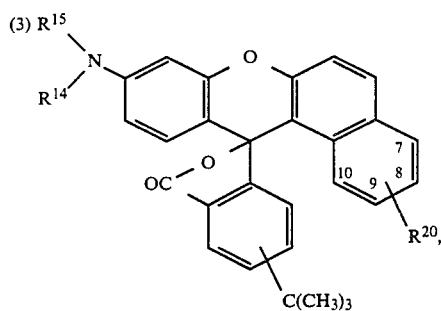

(3) (IV)

where $R^{14}$ and $R^{15}$ have the above meanings and $R^{20}$ is hydrogen, or is amino which is unsubstituted or monosubstituted or disubstituted by methyl, ethyl or benzyl and is in the 7-, 9- or 10-position.

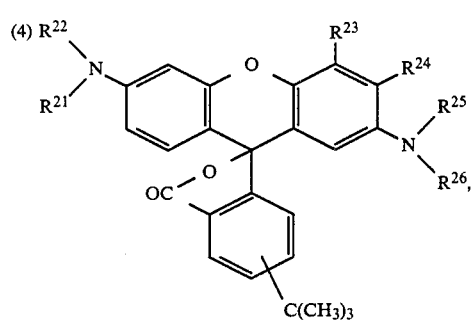

(4) (V)

where
$R^{21}$ is $C_1$–$C_4$-alkyl or $C_7$- or $C_8$-phenylalkyl,
$R^{22}$ is $C_1$–$C_4$-alkyl, $C_7$–$C_{10}$-phenylalkyl or $C_5$- or $C_6$-cycloalkyl, or is phenyl which is substituted by $C_1$–$C_4$-alkyl or chlorine, or $$-N\begin{matrix}R^{21}\\R^{22}\end{matrix}$$

is pyrrolidinyl, piperidinyl or morpholinyl,
$R^{23}$ is hydrogen or chlorine,
$R^{24}$ is hydrogen or methyl, and when $R^{23}$ is hydrogen then $R^{24}$ may furthermore be chlorine, and
$R^{25}$ is hydrogen, $C_1$–$C_4$-alkyl or $C_7$- or $C_8$-phenylalkyl, and
$R^{26}$ is hydrogen, $C_1$–$C_{12}$-alkyl, $C_7$–$C_{10}$-phenylalkyl, or $C_5$ or $C_6$-cycloalkyl, or is phenyl which is unsubstituted or substituted by chlorine, $C_1$–$C_4$-alkyl, methoxy, ethoxy, $C_1$- or $C_2$-alkylcarbonyl, benzoyl or phenoxy, or $$-N\begin{matrix}R^{25}\\R^{26}\end{matrix}$$

is pyrrolidinyl, piperidinyl or morpholinyl.

Because of their performance characteristics, the following compounds are particularly noteworthy:

(a) Fluorans of the formula (II) where

| | $R^1$ | $R^{10}$ | $R^{11}$ | $R^{12}$ | $R^{13}$ | $R^{27}$ |
|---|---|---|---|---|---|---|
| (a1) | —$CH_3$ | —$C_2H_5$ | —H | —$CH_3$ | —H | —H |
| (a2) | —$CH_3$ | —$C_2H_5$ | —$CH_3$ | —$CH_3$ | —H | —H |
| (a3) | —$CH_3$ | —$C_2H_5$ | —H | —$CH_3$ | —$CH_3$ | —H |
| (a4) | —H | 2-methylphenyl | —$CH_3$ | —$CH_3$ | —H | —H |
| (a5) | —H | 2,6-dimethylphenyl | —$CH_3$ | —$CH_3$ | —H | —H |
| (a6) | —H | 2,5-dimethylphenyl | —$CH_3$ | —$CH_3$ | —H | —H |
| (a7) | —H | 2-chlorophenyl | —$CH_3$ | —$CH_3$ | —H | —H |
| (a8) | —H | 4-chlorophenyl | —$CH_3$ | —$CH_3$ | —H | —H |
| (a9) | —H | 4-methoxyphenyl | —$CH_3$ | —$CH_3$ | —H | —H |
| (a10) | —$CH_3$ | —$C_2H_5$ | —H | —$CH_3$ | —H | —$CH_3$ |
| (a11) | —$CH_3$ | —$C_2H_5$ | —$CH_3$ | —Cl | —H | —H |
| (a12) | —$CH_3$ | —$C_2H_5$ | —H | —Cl | —H | —H |
| (a13) | —H | cyclohexyl | —Cl | —H | —H | —H |

(b) Fluorans of the formula (III) where $$-N\begin{matrix}R^{14}\\R^{15}\end{matrix}$$

| | | $R^{16}$ | $R^{17}$ | $R^{18}$ | $R^{19}$ |
|---|---|---|---|---|---|
| (b1) | —$N(CH_3)_2$ | —H | —H | —$C(CH_3)_3$ | —H |
| (b2) | —$N(C_2H_5)_2$ | —H | —H | —$C(CH_3)_3$ | —H |
| (b3) | 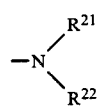 pyrrolidinyl | —H | —H | —$C(CH_3)_3$ | —H |
| (b4) | 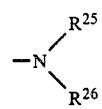 morpholinyl | —H | —H | —$C(CH_3)_3$ | —H |
| (b5) | —$N(CH_3)_2$ | —H | —H | —Cl | —H |
| (b6) | —$N(C_2H_5)_2$ | —H | —H | —Cl | —H |
| (b7) | —$N(C_2H_5)_2$ | —H | —H | —$OCH_3$ | —H |

-continued

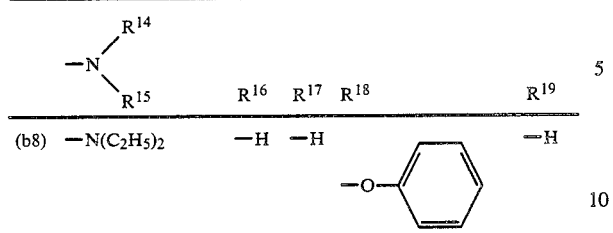

| | $R^{14}$, $R^{15}$ | $R^{16}$ | $R^{17}$ | $R^{18}$ | $R^{19}$ |
|---|---|---|---|---|---|
| (b8) | —N(C$_2$H$_5$)$_2$ | —H | —H | —O—C$_6$H$_5$ | —H |

(c) Fluorans of the formula (IV) where

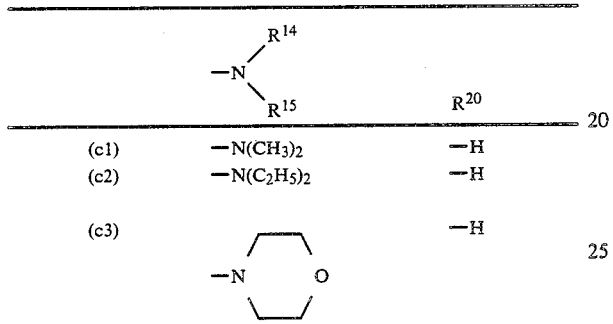

| | $R^{14}$, $R^{15}$ | $R^{20}$ |
|---|---|---|
| (c1) | —N(CH$_3$)$_2$ | —H |
| (c2) | —N(C$_2$H$_5$)$_2$ | —H |
| (c3) | —N(morpholino) | —H |

(d) Fluorans of the formula (V) where

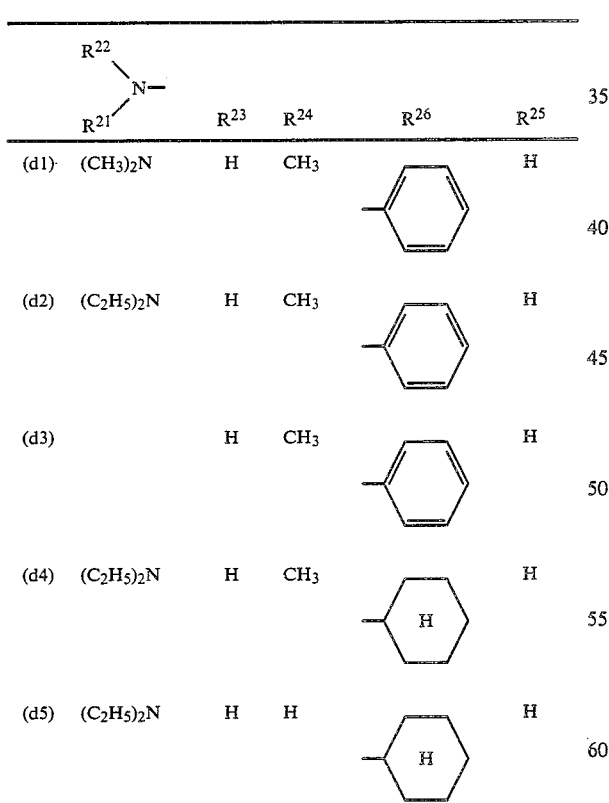

| | $R^{22}$, $R^{21}$ | $R^{23}$ | $R^{24}$ | $R^{26}$ | $R^{25}$ |
|---|---|---|---|---|---|
| (d1) | (CH$_3$)$_2$N | H | CH$_3$ | phenyl | H |
| (d2) | (C$_2$H$_5$)$_2$N | H | CH$_3$ | phenyl | H |
| (d3) | | H | CH$_3$ | phenyl | H |
| (d4) | (C$_2$H$_5$)$_2$N | H | CH$_3$ | cyclohexyl | H |
| (d5) | (C$_2$H$_5$)$_2$N | H | H | cyclohexyl | H |

The compounds of the general formula (I) can be prepared by a conventional process.

They can be synthesized by, for example, reacting an o-hydroxybenzophenone derivative of the formula

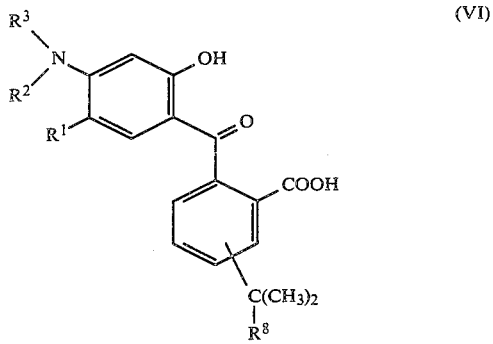
(VI)

with a phenol derivative of the formula

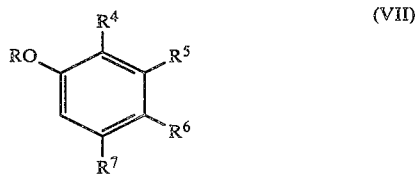
(VII)

or an o-hydroxybenzophenone of the formula

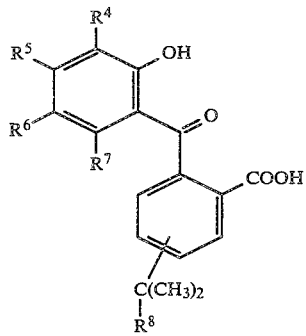
(VIII)

with an aniline compound of the formula

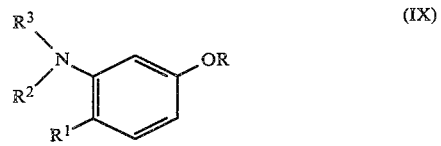
(IX)

In the formulae (VII) and (IX), R is hydrogen or C$_1$–C$_4$-alkyl, preferably hydrogen, methyl or ethyl, and in the formulae (VI) to (IX), R$^1$ to R$^8$ have the above meanings.

The reaction is advantageously carried out at from 10° to 130° C., in the presence of an acidic condensing agent, such as acetic acid, acetic anhydride, sulfuric acid, zinc chloride or phosphorus oxychloride.

The benzophenone derivatives (VI) and (VIII) are obtained by a conventional process, by reacting a phthalic anhydride of the formula

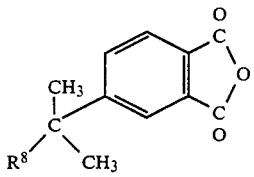

(X)

with an aniline compound of the formula (IX) or with a phenol of the formula (VII). The reaction is advantageously carried out in an inert organic solvent, such as toluene, xylene, chlorobenzene or dichlorobenzene, in the presence or absence of a condensing agent, such as zinc chloride or aluminum chloride. The reaction gives a mixture of the 4- and 5-tert.-butyl benzophenone compounds.

The Examples which follow illustrate the preparation of the fluorans. Parts and percentages are by weight.

EXAMPLE 1

16 parts of phosphorus oxychloride are added dropwise to a solution of 46.5 parts of 2-(2'-hydroxy-5'-methyl-benzoyl)-4-tert.-butylbenzoic acid (obtained by reacting 4-tert.-butylphthalic anhydride with 4-methylphenol) in 160 parts of chloroform. The mixture is stirred for 4 hours at room temperature, after which 22.5 parts of 3-ethylamino-4-methylphenol are added, and the mixture is refluxed for 3 hours. 150 parts of water are added, after which the chloroform is distilled off, and the oily residue is stirred in 100 parts of 25% strength ammonia water and 100 parts of toluene. The toluene phase is separated off, and evaporated down to 1/5 of its volume.

By adding 26 parts of methanol, 26 parts of 2,7-dimethyl-3-ethylamino-5'(6')-tert.-butylfluoran are precipitated:

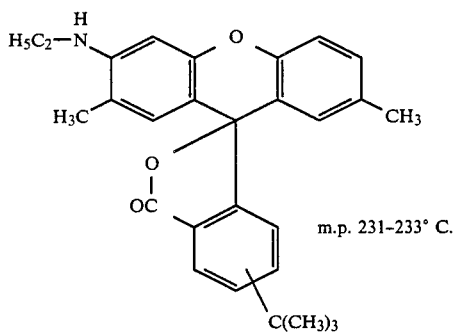

m.p. 231–233° C.

If a solution of the fluoran in partially hydrogenated terphenyl is enclosed in microcapsules, for example by the method described in EP-B 26 914, Example 1, and the microcapsules are applied onto paper, an intense orange copy is obtained when the paper is placed on an acceptor page and written on.

EXAMPLE 2

99 parts of 2-(2'-hydroxy-4',5'-dimethylbenzoyl)-4(5)-tert.-butylbenzoic acid and 45 parts of 3-ethylamino-4-methylphenol are reacted by a method similar to that described in Example 1 to give the color-producing agent of the formula

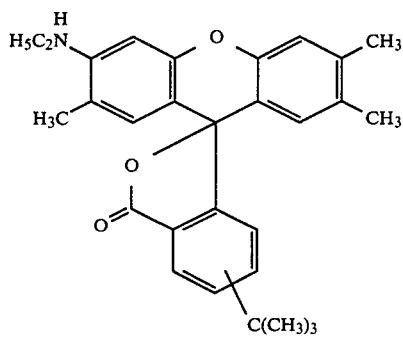

20 parts of 2,6,7-trimethyl-3-ethylamino-5'(6')-tert.-butylfluoran of melting point 247°–249° C. are obtained. When in contact with electron acceptors, the substance produces an orange coloration.

EXAMPLES 3 TO 16

Color-producing agents of the formula

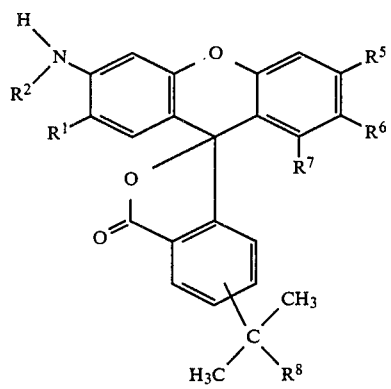

(Ia)

are obtained by a method similar to that described in Example 1. The meanings of the substituents are given in the table below, the hue produced in contact with electron acceptors being shown in the right-hand column.

| Example No. | $R^1$ | $R^2$ | $R^5$ | $R^6$ | $R^7$ | $R^8$ | Hue | m.p. [°C.] |
|---|---|---|---|---|---|---|---|---|
| 3 | $CH_3$ | $C_2H_5$ | H | $CH_3$ | H | $C_2H_5$ | orange | |
| 4 | $CH_3$ | $C_2H_5$ | H | $CH_3$ | H | $CH_2C(CH_3)_3$ | orange | |
| 5 | $CH_3$ | $C_2H_5$ | $C_2H_5$ | H | $C_2H_5$ | $CH_3$ | orange | |
| 6 | $CH_3$ | $C_2H_5$ | H | $C(CH_3)_3$ | H | $CH_3$ | orange | 220–222 |
| 7 | $CH_3$ | H | H | $CH_3$ | H | $CH_3$ | yellowish orange | |
| 8 | $CH_3$ | $C_2H_5$ | Cl | H | H | $CH_3$ | reddish orange | |
| 9 | H | i-$C_3H_7$ | H | $CH_3$ | H | $CH_3$ | orange | |
| 10 | H | i-$C_6H_{11}$ | H | $CH_3$ | H | $CH_3$ | orange | |

-continued

| Example No. | R¹ | R² | R⁵ | R⁶ | R⁷ | R⁸ | Hue | m.p. [°C.] |
|---|---|---|---|---|---|---|---|---|
| 11 | H | 2-methylphenyl | H | CH₃ | H | CH₃ | reddish brown | |
| 12 | H | 2,6-diethylmethylphenyl (2-C₂H₅, 6-CH₃) | CH₃ | CH₃ | H | CH₃ | reddish orange | |
| 13 | H | 2,5-dimethylphenyl | CH₃ | CH₃ | H | CH₃ | reddish orange | |
| 14 | H | 2-chlorophenyl | CH₃ | CH₃ | H | CH₃ | reddish orange | |
| 15 | H | 4-chlorophenyl | CH₃ | CH₃ | H | CH₃ | red | |
| 16 | H | 4-methoxyphenyl | CH₃ | CH₃ | H | CH₃ | red | |
| 17 | CH₃ | C₂H₅ | H | Cl | H | CH₃ | orange | 226–228 |
| 18 | H | -Cyclohexyl | Cl | H | H | CH₃ | orange | 296–298 |
| 19 | H | —C₂H₄—phenyl | CH₃ | Cl | H | CH₃ | reddish orange | 240–242 |
| 20 | CH₃ | C₂H₅ | CH₃ | H | H | CH₃ | orange | |

EXAMPLE 21

34 parts of 2-(2'-hydroxy-4'-dimethylaminobenzoyl)-4(5)-tert.-butylbenzoic acid and 15 parts of 4-tert.-butylphenol in 100 parts of 80% strength sulfuric acid are heated at 100° C. for 6 hours. The reaction mixture is poured onto 200 parts of ice and 200 parts of methanol, and is rendered alkaline with 25% strength ammonia water. The crystalline product is isolated, and further purification is carried out by stirring the product in 250 parts of toluene, 200 parts of water and 50 parts of 25% strength ammonia water, and separating phase and evaporating down to 1/5 of its initial volume. By adding 50 parts of ethanol, 13 parts of 3-dimethylamino-7,5'(6')-bis-tert.-butylfluoran of the formula

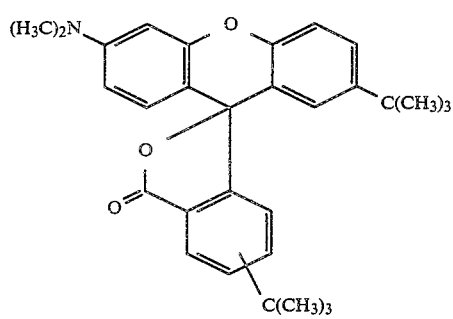

are precipitated from this solution, the product having a melting point of 185°–187° C. On electron acceptors, a reddish orange coloration is obtained.

EXAMPLE 22

34 parts of 2-(2'-hydroxy-4'-dimethylaminobenzoyl)4(5)-tert.-butylbenzoic acid are reacted with 11 parts of 4-methylphenol and the product is isolated, these steps being carried out similarly to Example 21. 21 parts of 3-dimethylamino-7-methyl-5'(6')-tert.-butylfluoran of the formula

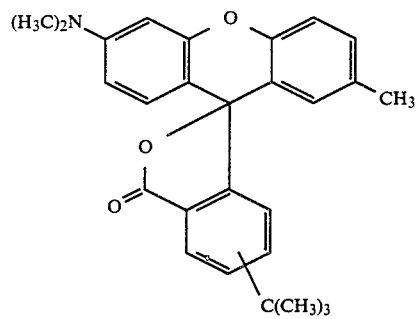

are obtained, the product having a melting point of 135°–140° C. On electron acceptors, a reddish orange coloration is obtained.

EXAMPLE 23

17 parts of 2-(2'-hydroxy-4'-dimethylaminobenzoyl)4(5)-tert.-butylbenzoic acid are reacted with 7.5 parts of 2-tert.-butylphenol and the product is isolated, these steps being carried out similarly to Example 21. 4 parts of 3-dimethylamino-5,5'(6')-bis-tert.-butylfluoran of the formula

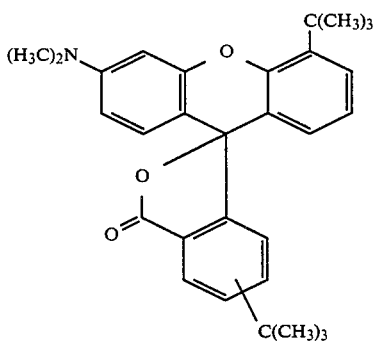

are obtained, the product having a melting point of 197°–199° C. In contact with acidic substances, a reddish orange coloration is obtained.

EXAMPLE 24

37 parts of 2-(2'-hydroxy-4'-diethylaminobenzoyl)4(5)-tert.-butylbenzoic acid are reacted with 12 parts of 3,4-dimethylphenol by a method similar to that described in Example 21. 14 parts of 3-diethylamino-6(8), 7-dimethyl-5'(6')-tert.-butylfluoran of the formula

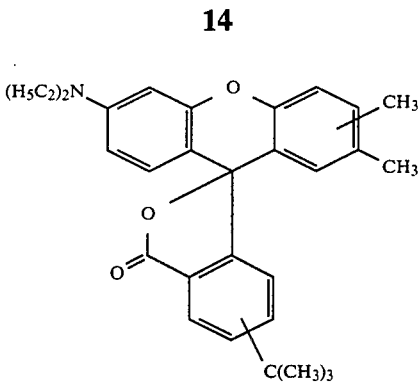

are obtained, the product having a melting point of 171°–173° C. In contact with acidic substances, a reddish orange coloration is obtained.

EXAMPLE 25

18.5 parts of 2-(2'-hydroxy-4'-diethylaminobenzoyl)-4(5)-tert.-butylbenzoic acid and 7.5 parts of 3,5-diethylphenol are reacted by a method similar to that described in Example 21 to give 2.5 parts of 3-diethylamino-6,8-diethyl-5'(6')-tert.-butylfluoran of the formula

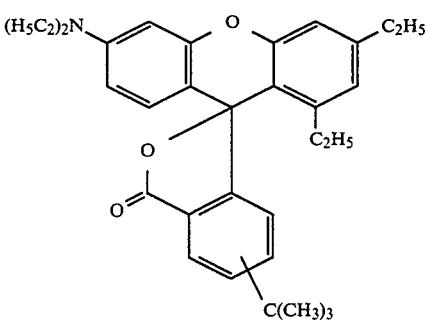

the product having a melting point of 185°–186° C. In contact with electron acceptors, the fluoran produces a reddish orange coloration, and its tendency to migrate is substantially smaller than that of the compound which is not substituted by a tert.-butyl group.

EXAMPLE 26

18 parts of 2-(2'-hydroxy-4'-diethylaminobenzoyl)4(5)-tert.-butylbenzoic acid are reacted with 6 parts of p-chlorophenol by a method similar to that described in Example 21. 7 parts of 3-diethylamino-7-chloro-5'(6')-tert.-butylfluoran of the formula

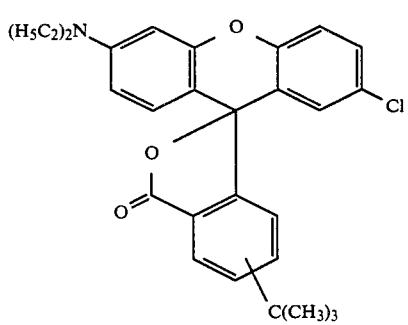

are obtained, the product having a melting point of 180°–182° C. In contact with electron acceptors, a red coloration is obtained.

EXAMPLE 27

37 parts of 2-(2'-hydroxy-4'-diethylaminobenzoyl)4(5)-tert.-butylbenzoic acid are reacted with 18 parts of p-phenoxyphenol by a method similar to that described in Example 21. 3 parts of 3-diethylamino-7-phenoxy-5'(6')-tert.-butylfluoran of the formula

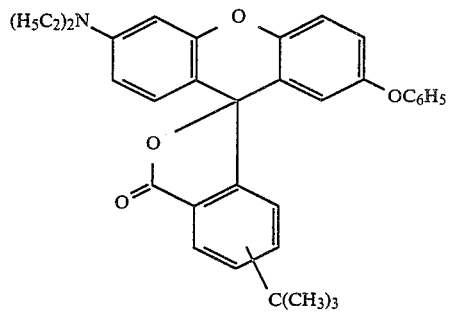

are obtained, the product having a melting point of 195°–198° C. In contact with electron acceptors, a red coloration is obtained.

EXAMPLE 28

37 parts of 2-(2'-hydroxy-4'-diethylaminobenzoyl)4(5)-tert.-butylbenzoic acid are reacted with 14 parts of 3-methyl-4-chlorophenol by a method similar to that described in Example 21. 5 parts of 3-diethylamino-6(8)-methyl-7-chloro-5'(6')-tert.-butylfluoran of the formula

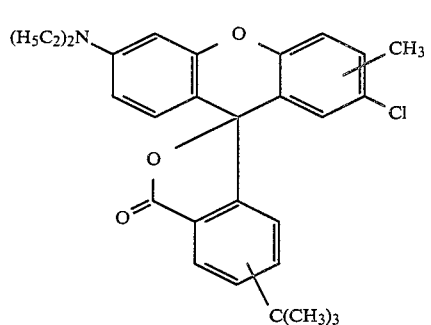

are obtained, the product having a melting point of 206°–211° C. In contact with electron acceptors, a reddish orange coloration is obtained.

EXAMPLE 29

37 parts of 2-(2'-hydroxy-4'-pyrrolidinobenzoyl)4(5)-tert.-butylbenzoic acid are reacted with 15 parts of 4-tert.-butylphenol by a method similar to that described in Example 21. 9 parts of 3-pyrrolidino-7,5'(6')-di-tert.-butylfluoran of the formula

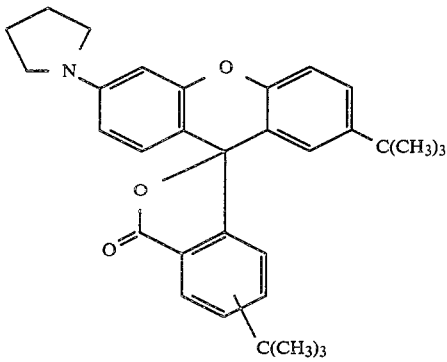

are obtained, the product having a melting point of 246°–248° C. In contact with acidic substances, a reddish orange coloration is obtained.

EXAMPLE 30

37 parts of 2-(2'-hydroxy-4'-pyrrolidinobenzoyl)-4(5)-tert.-butylbenzoic acid and 14.5 parts of β-naphthol in 250 parts of 50% strength sulfuric acid are refluxed for 8 hours, and the reaction mixture is worked up as described in Example 21. 6 parts of 3-pyrrolidino-7,8-benzo-5'(6')-tert.-butylfluoran of the formula

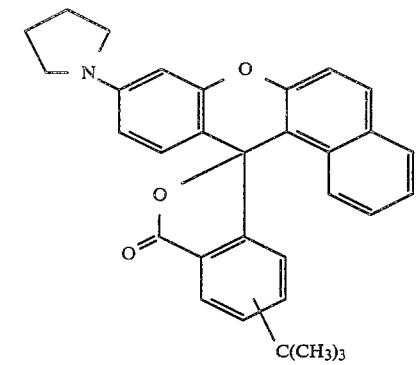

are obtained.

EXAMPLE 31

19 parts of 2-(2'-hydroxy-4'-morpholinobenzoyl)4(5)-tert.-butylbenzoic acid are reacted with 7.2 parts of β-naphthol by a method similar to that described in Example 21. 7 parts of 3-morpholino-7,8-benzo-5'(6')-tert.-butylfluoran of the formula

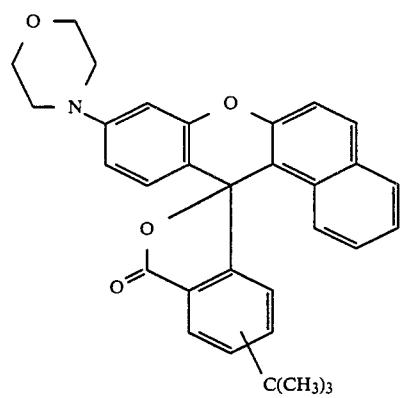

are obtained, the product having a melting point of 260°–267° C. On electron acceptors, a red coloration is obtained.

EXAMPLES 32 TO 67

Color-producing agents of the formula

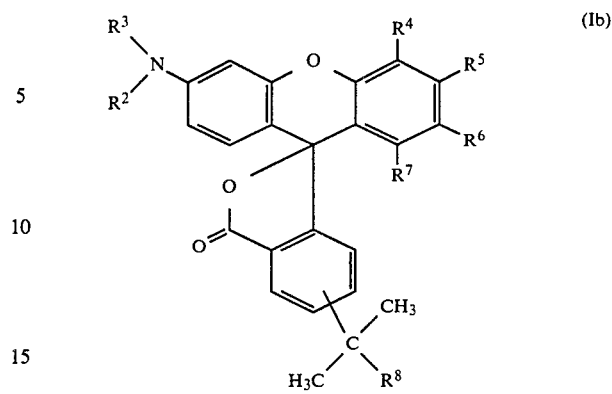

are prepared by a method similar to that described in Example 21. The meanings of the substituents $R^2$ to $R^8$ are given in the table below.

Contact with electron acceptors gives colorations having the hues shown in the right-hand column.

| Example No. | $R^2$ | $R^3$ | $R^4$ | $R^5$ | $R^6$ | $R^7$ | $R^8$ | Hue |
|---|---|---|---|---|---|---|---|---|
| 32 | $C_3H_7(n)$ | $C_3H_7(n)$ | H | H | $CH_3$ | H | $CH_3$ | reddish orange |
| 33 | $C_4H_9(n)$ | $C_4H_9(n)$ | H | H | $CH_3$ | H | $CH_3$ | reddish orange |
| 34 | —$(CH_2)_5$— | | H | H | $CH_3$ | H | $CH_3$ | reddish orange |
| 35 | $CH_3$ | $CH_3$ | —CH=CH—CH=CH— | | H | H | $CH_3$ | red |
| 36 | $CH_3$ | $CH_3$ | H | $CH_3$ | Cl | $CH_3$ | $CH_3$ | red |
| 37 | —$(CH_2)_4$— | | H | $C_2H_5$ | H | $C_2H_5$ | $CH_3$ | reddish orange |
| 38 | $CH_3$ | $CH_3$ | H | H | $CH_3$ | H | $CH_3$ | reddish orange |
| 39 | $CH_3$ | $CH_3$ | H | H | $CH_3$ | H | $CH_3$ | reddish orange |
| 40 | —$(CH_2)_2O(CH_2)_2$— | | H | H | $C(CH_3)_3$ | H | $CH_3$ | reddish orange |
| 41 | $CH_3$ | $CH_3$ | H | $C(CH_3)_3$ | $CH_3$ | $C(CH_3)_3$ | $CH_3$ | reddish orange |
| 42 | $C_2H_4OCH_3$ | $C_2H_4OCH_3$ | H | H | $CH_3$ | H | $CH_3$ | reddish orange |
| 43 | $CH_3$ | $C_6H_5$ | H | H | $CH_3$ | H | $CH_3$ | reddish orange |
| 44 | $CH_3$ | p-$C_6H_4$—$CH_3$ | H | H | $CH_3$ | H | $CH_3$ | reddish orange |
| 45 | $CH_3$ | c-$C_6H_{11}$ | H | H | $CH_3$ | H | $CH_3$ | reddish orange |
| 46 | $C_2H_5$ | c-$C_6H_{11}$ | H | H | $CH_3$ | H | $CH_3$ | reddish orange |
| 47 | $C_2H_5$ | $C_2H_5$ | H | H | $C_6H_5$ | H | $CH_3$ | reddish orange |
| 48 | $C_2H_5$ | $C_2H_5$ | H | H | 7,8-CH=CH—CH=CH—, NH$_2$ | | $CH_3$ | blue |
| 49 | $C_2H_5$ | $C_2H_5$ | H | H | 7,8-C=CH—CH=CH—, N—CH$_2$C$_6$H$_5$, H | | $CH_3$ | blue |
| 50 | $C_2H_5$ | $C_2H_5$ | H | H | 7,8-C=CH—CH=CH—, N(CH$_2$C$_6$H$_5$)$_2$ | | $CH_3$ | blue |
| 51 | $C_2H_5$ | $C_2H_5$ | H | H | 7,8-C=CH—CH=CH—, N(CH$_3$)$_2$ | | $CH_3$ | blue |
| 52 | $C_2H_5$ | $C_2H_5$ | H | H | $C_8H_{17}(n)$ | H | $CH_3$ | reddish orange |
| 53 | $C_2H_5$ | $C_2H_5$ | H | H | $C_9H_{19}(n)$ | N | $CH_3$ | reddish orange |
| 54 | $CH_3$ | p-$C_6H_4$—Cl | H | H | $CH_3$ | H | $CH_3$ | reddish orange |
| 55 | $CH_2C_6H_5$ | $CH_2C_6H_5$ | H | H | $CH_3$ | H | $CH_3$ | reddish orange |
| 56 | $C_2H_5$ | $C_2H_5$ | i-$C_3H_7$ | H | H | $CH_3$ | $CH_3$ | reddish orange |
| 57 | o-$C_6H_4(CH_2)_2$ | | H | H | $CH_3$ | H | $CH_3$ | reddish orange |
| 58 | $C_2H_5$ | $C_2H_5$ | H | $C(CH_3)_3$ | $CH_3$ | $C(CH_3)_3$ | $CH_3$ | reddish orange |

-continued

| Example No. | R² | R³ | R⁴ | R⁵ | R⁶ | R⁷ | R⁸ | Hue |
|---|---|---|---|---|---|---|---|---|
| 59 | C₂H₅ | C₂H₅ | H | H | —CH(CH₃)C₂H₅ | H | CH₃ | reddish orange |
| 60 | C₂H₅ | C₂H₅ | Cl | H | Cl | H | CH₃ | reddish orange |
| 61 | C₂H₅ | C₂H₅ | H | H | CH₃ | H | C₂H₅ | reddish orange |
| 62 | C₂H₅ | C₂H₅ | H | H | CH₃ | H | CH₂C(CH₃)₃ | reddish orange |
| 63 | C₂H₅ | C₂H₅ | H | H | C₂H₄C₆H₅ | H | CH₃ | reddish orange |
| 64 | C₂H₅ | C₂H₅ | H | H | Br | H | CH₃ | red |
| 65 | C₂H₅ | C₂H₅ | Cl | H | Cl | H | CH₃ | red |
| 66 | C₂H₅ | C₂H₅ | H | H | OCH₃ | H | CH₃ | red |
| 67 | —(CH₂)₅— | | H | Cl | H | H | CH₃ | red | c = cyclo

EXAMPLES 68 TO 75

Color-producing agents of the formula (XI)

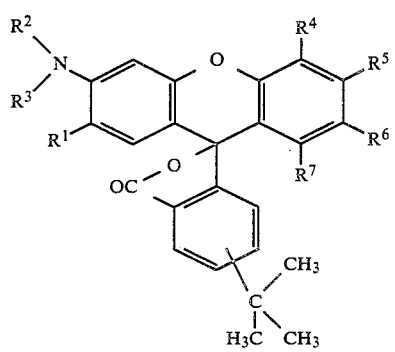

(XI)

are prepared by a method similar to that described in Example 21. The meanings of the substituents $R^2$ to $R^7$ are shown in the table below.

Contact with electron acceptors gives colorations having the hues shown in the right-hand column.

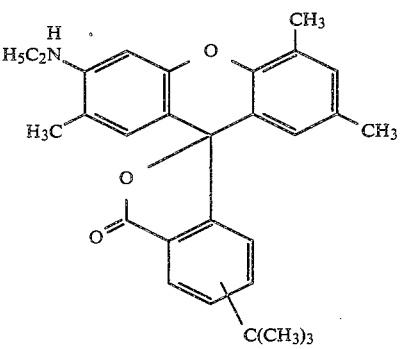

9 parts of 2,5,7-trimethyl-3-ethylamino-5'(6')-tert.-butylfluoran of melting point 258°–260° C. are obtained. In contact with electron acceptors, the compound produces an orange coloration.

EXAMPLE 77

18 parts of 2-(2'-hydroxy-4'-methyl-5'-chlorobenzoyl)-4(5)-tert.-butylbenzoic acid are reacted with 8

| Example No. | R² | R³ | R⁴ | R⁵ | R⁶ | R⁷ | Hue | m.p. [°C.] |
|---|---|---|---|---|---|---|---|---|
| 68 | —(CH₂)₂—O—(CH₂)₂— | | —H | —CH₃ | —CH₃ | —H | red | 90–92 |
| 69 | —CH₃ | —CH₃ | —H | —CH₃ | —Cl | —H | red | 188–190 |
| 70 | —(CH₂)₂—O—(CH₂)₂— | | —H | —CH₃ | —Cl | —H | red | 198–200 |
| 71 | —(CH₂)₅— | | —CH₃ | —H | —CH₃ | —H | red | 214–216 |
| 72 | —(CH₂)₅— | | —H | —CH₃ | —Cl | —H | red | 232–234 |
| 73 | —(CH₂)₅— | | —H | —CH₃ | —H | —CH₃ | red | 199–201 |
| 74 | —(CH₂)₅— | | —H | —H | —Cl | —H | red | 204–206 |
| 75 | —(CH₂)₅— | | —H | —Cl | —H | —H | red | 206–208 |

EXAMPLE 76

16 parts of 2-(2'-hydroxy-3',5'-dimethylbenzoyl)4(5)-tert.-butylbenzoic acid are reacted with 8 parts of 3-ethylamino-4-methylphenol by a method similar to that described in Example 1 to give the color-producing agent of the formula parts of 3-ethylamino-4-methylphenol by a method similar to that described in Example 1 to give the color-producing agent of the formula

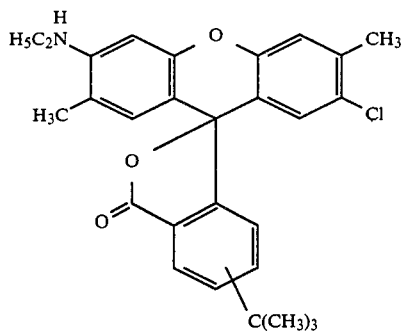
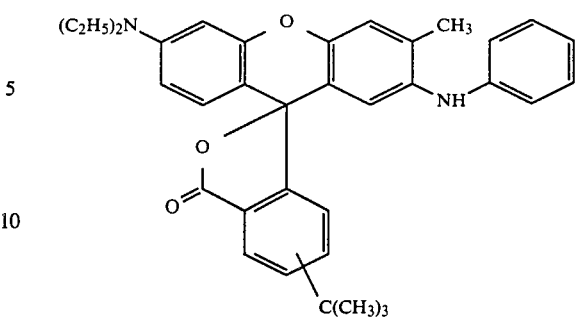

7 parts of 7-chloro-2,6-dimethyl-3-ethylamino-5'(6')-tert.-butylfluoran of melting point 186°–188° C. are obtained. In contact with electron acceptors, the substance produces an orange coloration.

EXAMPLE 78

24 parts of 2-(2'-hydroxy-4'-diethylaminobenzoyl)4(5)-tert.-butylbenzoic acid and 10.15 parts of 2-methyl-4-methoxydiphenylamine in 74 parts of 96% strength sulfuric acid are stirred for 36 hours at room temperature. The reaction solution is introduced into 750 parts of ice water, after which the precipitate formed is filtered off under suction and washed neutral with water. The product is dissolved in a mixture of 250 parts of toluene and 250 parts of 10% strength sodium hydroxide solution at 90° C., the aqueous phase is separated off, and the toluene solution is extracted by shaking twice with 150 parts of 10% strength sodium hydroxide solution and once with 5% strength sodium chloride solution. The organic phase is evaporated down to half its volume, 18 parts of 3-diethylamino-6-methyl-7-phenylamino-5'(6')-tert.-butylfluoran of the formula crystallizing out. The compound melts at 247°–250° C. and, in contact with electron acceptors, gives an intense black coloration.

EXAMPLES 79 TO 102

Color-producing agents of the formula (XII)

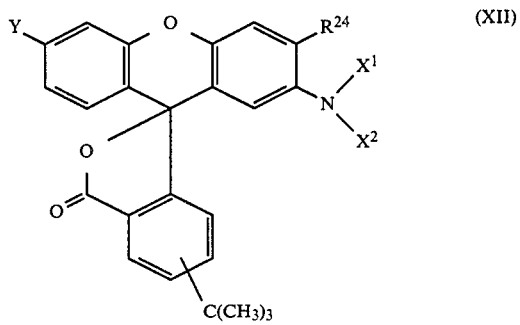

are obtained by a method similar to that described in Example 78, using the same molar ratios. The meanings of the substituents are shown in the table below.

| Example No. | Y | $R^{24}$ | $X^2$ | $X^1$ | m.p. | Hue |
|---|---|---|---|---|---|---|
| 79 | $(CH_3)_2N$ | $CH_3$ | phenyl | H | 185–189 | black |
| 80 | pyrrolidin-N— | $CH_3$ | phenyl | H | 245–248 | black |
| 81 | morpholin-N— | $CH_3$ | phenyl | H | 218–220 | greenish black |
| 82 | $(C_2H_5)_2N$ | H | cyclohexyl | H | 151–155 | olive |
| 83 | $(C_2H_5)_2N$ | H | $-CH(CH_3)_2$ | H | 218–221 | olive |

-continued

| Example No. | Y | R²⁴ | X² | X¹ | m.p. | Hue |
|---|---|---|---|---|---|---|
| 84 | (C₂H₅)N | CH₃ | 3-methylcyclohexyl | H | 172–175 | olive |
| 85 | pyrrolidin-1-yl | CH₃ | 3-methylcyclohexyl | H | 225–231 | olive |
| 86 | morpholin-4-yl | CH₃ | 3-methylcyclohexyl | H | 267–273 | olive |
| 87 | morpholin-4-yl | CH₃ | —CH(CH₃)₂ | H | 162–165 | olive |
| 88 | pyrrolidin-1-yl | CH₃ | H | H | | violet |
| 89 | pyrrolidin-1-yl | H | —C₂H₄—C₆H₅ | H | | olive |
| 90 | pyrrolidin-1-yl | H | —CH₂—C₆H₅ | H | | olive |
| 91 | pyrrolidin-1-yl | H | —CH(CH₃)₂ | H | | olive |
| 92 | pyrrolidin-1-yl | CH₃ | —CH(CH₃)₂ | H | | black |
| 93 | pyrrolidin-1-yl | H | —(CH₂)₄— | | | green |
| 94 | pyrrolidin-1-yl | H | —(CH₂)₅— | | | violet |
| 95 | —N(C₂H₅)₂ | Cl | —CH(CH₃)₂ | H | | black |
| 96 | —N(C₂H₅)₂ | Cl | cyclohexyl | H | | black |
| 97 | —N(CH₃)₂ | CH₃ | —CH(CH₃)₂ | H | | black |

-continued

| Example No. | Y | R²⁴ | X² | X¹ | m.p. | Hue |
|---|---|---|---|---|---|---|
| 98 | —N(CH₃)₂ | CH₃ | cyclohexyl | H | | black |
| 99 | —N(C₂H₅)(p-tolyl) | H | phenyl | CH₃ | | green |
| 100 | —N(CH₃)(p-tolyl) | CH₃ | phenyl | H | | black |
| 101 | pyrrolidino | H | —CH₂—C₆H₅ | —CH₂—C₆H₅ | | green |
| 102 | —N(C₂H₅)₂ | 5-Cl | cyclohexyl | H | | olive |

EXAMPLE 103

23 parts of 2-(2'-hydroxy-4'-pyrrolidinobenzoyl)4(5)-tert.-butylbenzoic acid and 8.5 parts of 2-methyl-4-methoxyisopropylaniline in 74 parts of 90% strength sulfuric acid are reacted for 6 hours at 70° C., and the mixture is worked up as described in Example 78. 10 parts of the color-producing agent of the formula

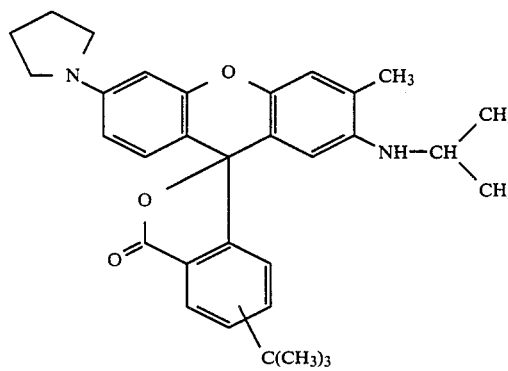

are obtained. In contact with electron acceptors, the compound gives an olive coloration.

Using the same procedure, color-producing agents of the formula (XII) containing the following radicals are obtained:

| Example No. | Y | R²⁴ | X² | X¹ | Hue |
|---|---|---|---|---|---|
| 104 | (CH₃)₂N | H | n-C₈H₁₇ | H | olive |
| 105 | (CH₃)₂N | H | p-tolyl | H | olive |
| 106 | (CH₃)₂N | H | o-tolyl | H | olive |
| 107 | (C₂H₅)N | CH₃ | CH₃ | H | olive |
| 108 | (C₂H₅)N | CH₃ | C₂H₅ | H | olive |
| 109 | (C₂H₅)N | CH₃ | n-C₄H₉ | H | olive |
| 110 | CH₃(cyclohexyl)N— | H | C₂H₅ | H | olive |
| 111 | CH₃(cyclohexyl)N— | CH₃ | C₂H₅ | H | olive |
| 112 | (CH₃)₂N | H | CH₂C₆H₅ | CH₂C₆H₅ | olive |
| 113 | (C₂H₅)₂N | CH₃ | n-C₃H₇ | CH₃ | olive |
| 114 | (C₂H₅)₂N | CH₃ | H | H | reddish brown |

We claim:

1. A fluoran of the formula

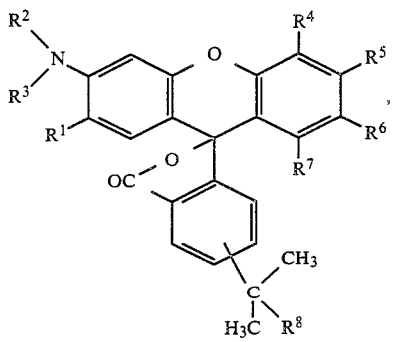

where
$R^1$ is hydrogen or methyl,
$R^2$ is hydrogen, $C_1$-$C_4$-alkyl, $C_7$- or $C_8$-phenylalkyl, cyanoethyl, chloroethyl or alkoxyalkyl having a total of 3 to 5 carbon atoms,
$R^3$ is hydrogen, $C_1$-$C_4$-alkyl, $C_7$-$C_{10}$-phenylalkyl, $C_5$- or $C_6$-cycloalkyl, cyanoethyl, chloroethyl, alkoxyalkyl having a total of 3 to 5 carbon atoms, or phenyl which is unsubstituted or substituted by $C_1$-$C_4$-alkyl, methoxy, chlorine or bromine, or

is N-pyrrolidinyl, N-piperidinyl, N-morpholinyl or N-isoindolinyl,
$R^4$ and $R^5$ independently of one another are each hydrogen, $C_1$-$C_4$-alkyl, $C_1$-$C_4$-alkoxy or halogen,
$R^6$ is hydrogen, halogen, $C_1$-$C_{12}$-alkyl, $C_1$-$C_4$-alkoxy, $C_7$-$C_{10}$-phenylalkoxy, phenoxy, phenyl, or a group of the formula

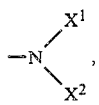

where $X^1$ is hydrogen, $C_1$-$C_4$-alkyl, chloroethyl, alkoxyalkyl having a total of 3 to 5 carbon atoms, $C_7$- or $C_8$-phenylalkyl and $X^2$ is hydrogen, $C_1$-$C_{12}$-alkyl, chloroethyl, $C_5$- or $C_6$-cycloalkyl, alkoxyalkyl having a total of 3 to 5 carbon atoms, $C_7$-$C_{10}$-phenylalkyl, or phenyl which is unsubstituted or substituted by halogen, $C_1$-$C_4$-alkyl, $C_1$-$C_4$-alkoxy, $C_1$-$C_4$-alkylcarbonyl, benzoyl or phenoxy, or is $C_1$-$C_4$-alkoxycarbonyl-$C_1$-$C_3$-alkyl, or carbamyl-$C_1$-$C_3$-alkyl, or

is pyrrolidinyl, piperidinyl or morpholinyl,
$R^7$ is hydrogen, $C_1$-$C_4$-alkyl or halogen and
$R^8$ is $C_1$-$C_5$-alkyl, and the radicals $R^4$ and $R^5$ and/or $R^6$ and $R^7$ together can each be a —CH=CH—CH=CH— bridge, and the fused-on ring can be unsubstituted or substituted by halogen or by amino which is unsubstituted or monosubstituted or disubstituted by $C_1$-$C_4$-alkyl or $C_7$- or $C_8$-phenylalkyl.

2. A fluoran as claimed in claim 1, wherein $R^8$ is methyl, ethyl or —$CH_2$—$C(CH_3)_3$.

3. A fluoran as claimed in claim 1, of the formula

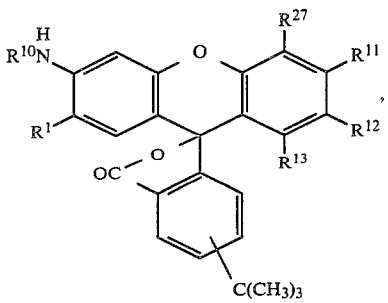

where
$R^1$ is hydrogen or methyl,
$R^{10}$ is hydrogen, $C_1$-$C_4$-alkyl, cyclohexyl or benzyl, or is phenyl which is unsubstituted or substituted by methyl, ethyl, chlorine, bromine or methoxy, the number of substituents being 1, 2 or 3,
$R^{11}$ is hydrogen, chlorine, or $C_1$-$C_4$-alkyl,
$R^{12}$ is $C_1$-$C_{12}$-alkyl or halogen, and
$R^{13}$ and $R^{27}$ are each hydrogen or methyl.

4. A fluoran as claimed in claim 3, wherein $R^1$ is hydrogen and $R^{10}$ is phenyl which is monosubstituted or disubstituted by methyl or ethyl and may be further monosubstituted by chlorine, bromine or methoxy.

5. A fluoran of the formula

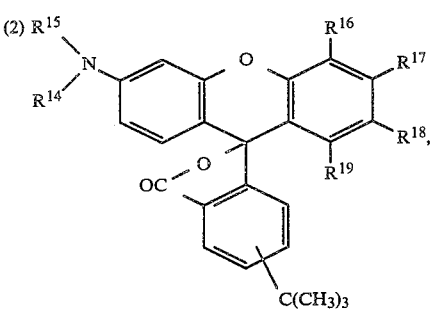

where
$R^{14}$ is $C_1$-$C_4$-alkyl, $C_7$- or $C_8$-phenylalkyl or alkoxyalkyl having a total of 3 to 5 carbon atoms,
$R^{15}$ is $C_1$-$C_4$-alkyl, $C_7$-$C_{10}$-phenylalkyl, $C_5$- or $C_6$-cycloalkyl or alkoxyalkyl having a total of 3 to 5 carbon atoms, or is phenyl which is unsubstituted or monosubstituted by $C_1$-$C_4$-alkyl, chlorine or bromine, or

is pyrrolidinyl, piperidinyl or morpholinyl,
$R^{16}$ and $R^{17}$ independently of one another are each hydrogen, chlorine or $C_1$-$C_4$-alkyl,
$R^{18}$ is hydrogen, $C_1$-$C_{12}$-alkyl, $C_1$-$C_4$-alkoxy, $C_7$-$C_{10}$-phenylalkoxy, phenoxy or halogen, and $R^{19}$ is hydrogen or $C_1$–$C_4$-alkyl.

6. A fluoran as claimed in claim 1, of the formula

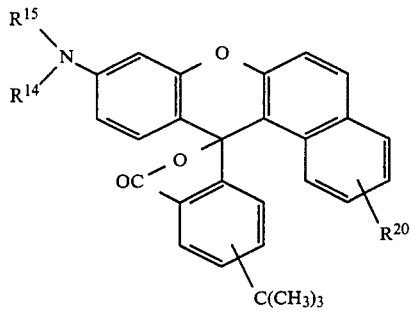

where $R^{14}$ is $C_1$–$C_4$-alkyl, $C_7$- or $C_8$-phenylalkyl or alkoxyalkyl having a total of 3 to 5 carbon atoms, $R^{15}$ is $C_1$–$C_4$-alkyl, $C_7$–$C_{10}$-phenylalkyl, $C_5$- or $C_6$-cycloalkyl or alkoxyalkyl having a total of 3 to 5 carbon atoms, or is phenyl which is unsubstituted or monosubstituted by $C_1$–$C_4$-alkyl, chlorine or bromine, or

is pyrrolidinyl, piperidinyl or morpholinyl, and $R^{20}$ is hydrogen, or amino which is unsubstituted or monosubstituted or disubstituted by methyl, ethyl or benzyl and is in the 7-, 9- or 10-position.

7. A fluoran of the formula

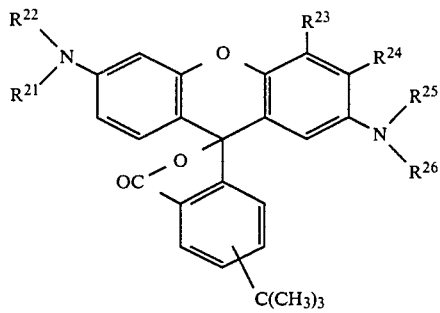

where $R^{21}$ is $C_1$–$C_4$-alkyl or $C_7$- or $C_8$-phenylalkyl, $R^{22}$ is $C_1$–$C_4$-alkyl, $C_7$–$C_{10}$-phenylalkyl or $C_5$- or $C_6$-cycloalkyl, or is phenyl which is substituted by $C_1$–$C_4$-alkyl or chlorine, or

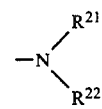

is pyrrolidinyl, piperidinyl or morpholinyl, $R^{23}$ is hydrogen or chlorine, $R^{24}$ is hydrogen or methyl, and when $R^{23}$ is hydrogen $R^{24}$ may furthermore be chlorine, and $R^{25}$ is hydrogen, $C_1$–$C_4$-alkyl or $C_7$- or $C_8$-phenylalkyl, and $R^{26}$ is hydrogen, $C_1$–$C_{12}$-alkyl, $C_7$–$C_{10}$-phenylalkyl or $C_5$ or $C_6$-cycloalkyl, or is phenyl which is unsubstituted or substituted by chlorine, $C_1$–$C_4$-alkyl, methoxy, ethoxy, $C_1$- or $C_2$-alkylcarbonyl, benzoyl or phenoxy, or

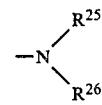

is pyrrolidinyl, piperidinyl or morpholinyl.

* * * * *